United States Patent [19]
Boag et al.

[11] 3,964,479
[45] June 22, 1976

[54] EXTRACORPOREAL BLOOD CIRCULATION SYSTEM AND DRIP CHAMBER WITH ADJUSTABLE BLOOD LEVEL

[75] Inventors: James T. Boag, Conifer; Brian E. Morgan, Wheatridge, both of Colo.

[73] Assignee: Cobe Laboratories, Inc., Lakewood, Colo.

[22] Filed: Nov. 20, 1974

[21] Appl. No.: 525,426

[52] U.S. Cl. .................. 128/214 R; 128/DIG. 3; 128/214 E; 23/258.5 R; 137/211.5; 210/90; 417/249
[51] Int. Cl.² .......................................... A61M 1/03
[58] Field of Search ........ 128/214 R, 214 C, 214 E, 128/214 F, 214.2, 227, DIG. 3; 210/89.90, 94, 321 K; 137/209, 211.5; 23/258.5; 417/249

[56] References Cited
UNITED STATES PATENTS

| | | | |
|---|---|---|---|
| 2,927,582 | 3/1960 | Berkman et al. | 128/DIG. 3 |
| 3,091,239 | 5/1963 | Moeller | 128/214 F |
| 3,543,752 | 12/1970 | Hesse et al. | 128/214 E |
| 3,756,234 | 9/1973 | Kopp | 128/214 R |
| 3,844,283 | 10/1974 | Dabney | 128/214 C |
| 3,848,592 | 11/1974 | Willock | 128/214 R |

FOREIGN PATENTS OR APPLICATIONS 1,182,016   2/1970   United Kingdom............ 128/214 C

*Primary Examiner*—Dalton L. Truluck
*Attorney, Agent, or Firm*—Reising, Ethington, Barnard, Perry & Brooks

[57] ABSTRACT

In accordance with the invention there is provided an extracorporeal blood circulation system including a drip chamber having a blood inlet in its top and a blood outlet in its bottom, such chamber during operation containing blood in its bottom portion and air in its top portion, an air passage communicating with the top of the chamber, an air pump communicating with the atmosphere and with the passage for pumping air through the passage from the chamber into the atmosphere and from the atmosphere into the chamber, and means for selectively actuating the pump to either pump air into or out of the chamber.

3 Claims, 4 Drawing Figures

EXTRACORPOREAL BLOOD CIRCULATION SYSTEM AND DRIP CHAMBER WITH ADJUSTABLE BLOOD LEVEL

The subject matter of the present invention is an extracorporeal blood circulation system having improved means for removing any air bubbles from the blood.

Extracorporeal blood circulation systems are used, for example, for circulating a medical patient's blood through, for example, an artificial kidney. Such a system comprises a tube for withdrawing blood from the patient to the artificial kidney, the artificial kidney itself, and a tube for returning the blood from the artificial kidney to the patient. One or more pumps are used in the system to augment the heart of the patient in causing circulation of the blood through the system. Such systems include various other components, one of which is to assure that the blood returned to the patient does not include any air bubbles. For this purpose it is conventional to use in the system what is referred to in the art as a drip chamber. A drip chamber comprises a chamber, preferably of transparent material, with a blood inlet at the top thereof and a blood outlet at the bottom, the bottom portion of the chamber containing a pool of the patient's blood and the top portion of the chamber containing air. The blood flows from the inlet into the pool of blood. Because the chamber has a cross-section much greater than that of the tubing forming the inlet and the outlet, the rate of flow of the blood in the pool within the chamber is much slower than the rate of flow in the tubing. Hence, while the blood is in the chamber any air bubbles in the blood can rise to the surface of the blood within the chamber and enter into the air mass in the upper portion of the chamber. The result is that the blood contains no air bubbles as it exits from the chamber at the bottom end thereof.

To assure that the drip chamber remains operative it is necessary that the blood within the chamber be maintained within limits. That is, if there were no air in the top portion of the chamber, or if the entire chamber were filled with air, then the chamber would not perform its intended function. Typically, the blood level in the chamber is such that the blood fills from about one-third to three-fourths of the vertical height of the chamber and with the remaining portion being the air at the top of the chamber.

Heretofore it has been conventional practice to provide the top of the chamber with a plug of resilient needle-penetrable material such that the medical attendant can insert, through the plug, the needle of a syringe thereby to either insert air into the chamber or withdraw air from the chamber, whichever might be needed for putting the blood level in the chamber within the desired limits. Such structure and procedure are undesirable, for one reason because the use of a hypodermic needle and syringe is necessitated. Even skilled medical attendants dislike frequent use of a hypodermic needle because of the always present hazard of the medical attendant accidentally puncturing his or her own hand — and with resultant threat of infection such as hepatitis. But for an artificial kidney blood circulation system for use by the patient without benefit of a skilled medical attendant, all the more so is there a hazard in seeking to establish and maintain the blood level in the drip chamber by the use of a hypodermic needle and syringe.

The present invention solves the aforesaid problem. That is, by way of the present invention the blood level in the drip chamber can be initially established and then maintained within the desired limits conveniently and without hazard, whether by a skilled medical attendant or by the patient.

Briefly, the blood circulation system of the present invention includes a drip chamber, an air passage in communication with the upper air-filled portion of the chamber and in communication with an air pump for pumping air from the atmosphere into the chamber or vice versa, and means for selectively actuating the air pump either to pump air into the chamber or remove air from the chamber. In the preferred embodiment the air pump comprises one or more rollers biased against and rollable along a flexible tube to fully collapse it in the area of contact of the roller to thereby pump air through the tube in the direction of the movement of the roller. Still further, in the most preferred embodiment the air passage contains a hydrophobic filter, i.e. a filter which allows the passage of air but does not allow the passage of blood or other liquid, thereby to assure against any flow of blood or other liquid through the passage beyond the hydrophobic filter.

Other features and advantages of the invention will appear more clearly from the following description of the most preferred embodiment thereof, which description is made with reference to the drawings in which.

Figure 1:
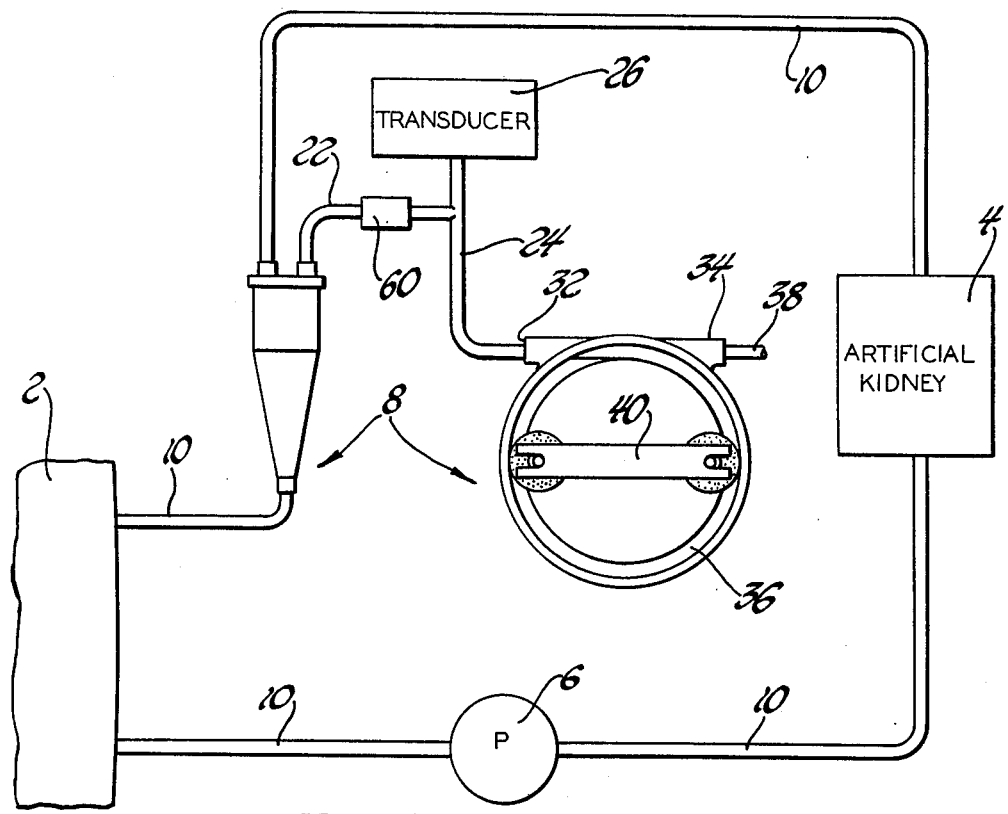
FIG. 1 is a schematic showing of an extracorporeal blood circulation system incorporating the present invention.
Figure 2:
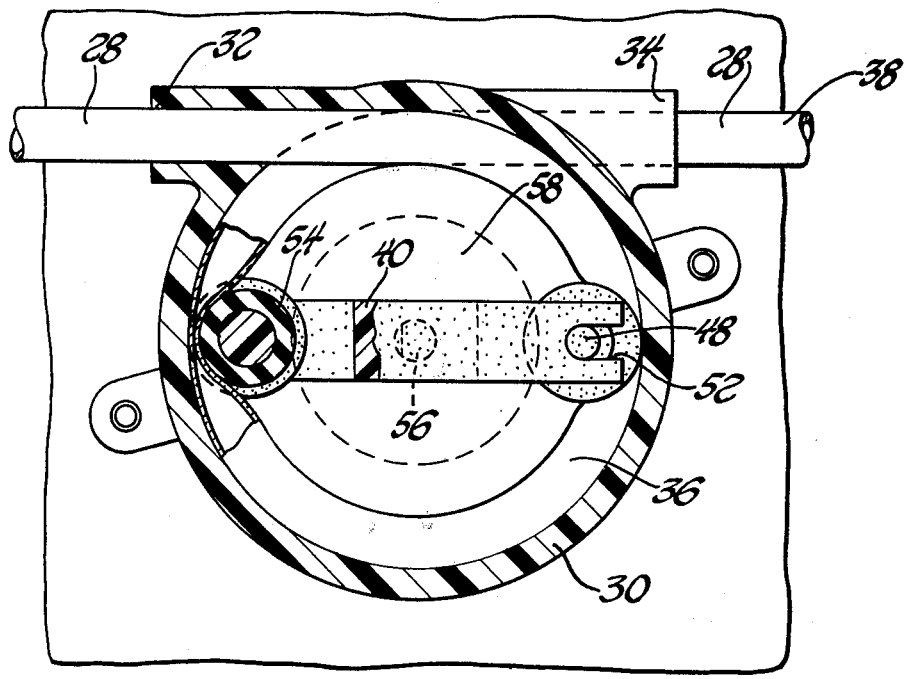
FIG. 2 is a view taken on the line 2—2 of FIG. 3.
Figure 3:
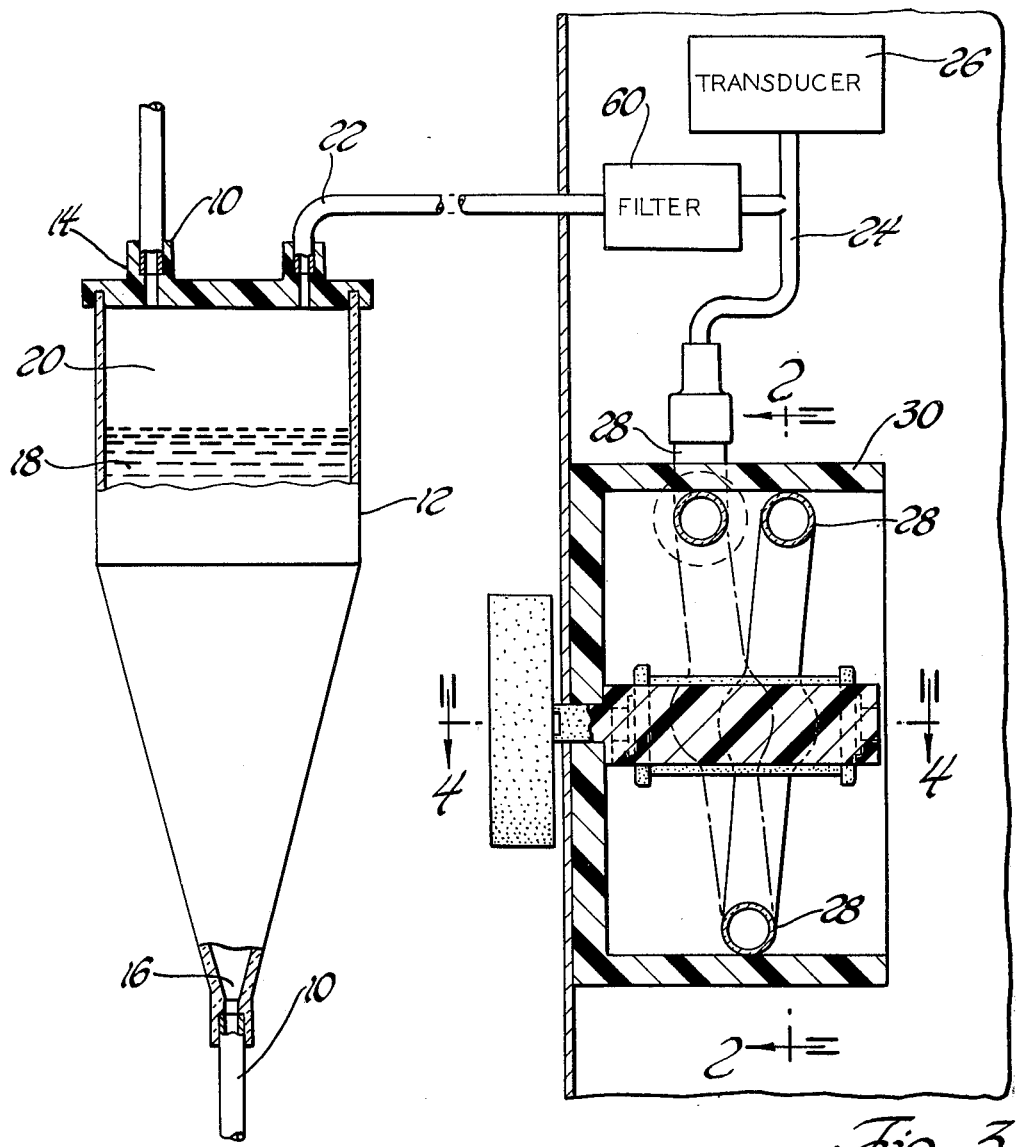
FIG. 3 is a side view in partial cross-section showing the drip chamber and associated components of the system shown in FIG. 1.

Referring now to FIG. 1, the reference numeral 2 depicts the body of the patient, 4 is an artificial kidney, 6 represents pumping means in the system for pumping the patient's blood therethrough, and 8 is the device as hereinafter more fully described, for removing air bubbles from the blood prior to its return to the patient. Flexible tubing 10 conducts the blood from the patient's body through the components and then back into the patient's body. As has been indicated previously, such systems generally contain additional components such for example as an air bubble detector, a heparin pump, and an alarm device actuated by abnormalities as, for example, in the blood pressure of the system.

Referring further now to the drawings, the device 8 comprises a drip chamber 12, preferably formed of a transparent organic resin, having a blood inlet 14 at the top thereof and a blood outlet 16 at the bottom. A piece of the tubing 10 joins to the inlet and another piece of the tubing 10 joins to the outlet. The chamber is of elongated shape, arranged with its longitudinal axis vertical, so that blood entering into the chamber drips toward the bottom of the chamber by force of gravity, and has a cross-section considerably greater than that of the tubing of the inlet and outlet. During operation, which will be described further hereinafter, the bottom portion of the chamber contains a pool 18 of the patient's blood and the blood entering the chamber from the inlet falls into the pool of blood 18. The upper portion of the chamber is filled with air 20.

Secured to and communicating with the upper end of the chamber is an air passage comprising tube 22 which joins to a tube 24 the upper end of which, as shown, communicates with a transducer 26 for measuring the pressure within the drip chamber and the lower end of which tube 24 communicates with a roller type air pump comprising a flexible tube 28 which can, for example, be of plasticized polyvinyl chloride and which is preferably of larger diameter than that of the tubes 22 and 24. The tube 28 extends into a cylindrical housing 30 through an opening 32 and exits from the housing through opening 34 the axis of which is lateral to that of the opening 32. The center portion 36 of the tube 28 extends through 360° and abuts the inner cylindrical wall of the housing. Free end 38 of the tube 28 is open and hence communicates with the ambient atmosphere.

Figure 4:
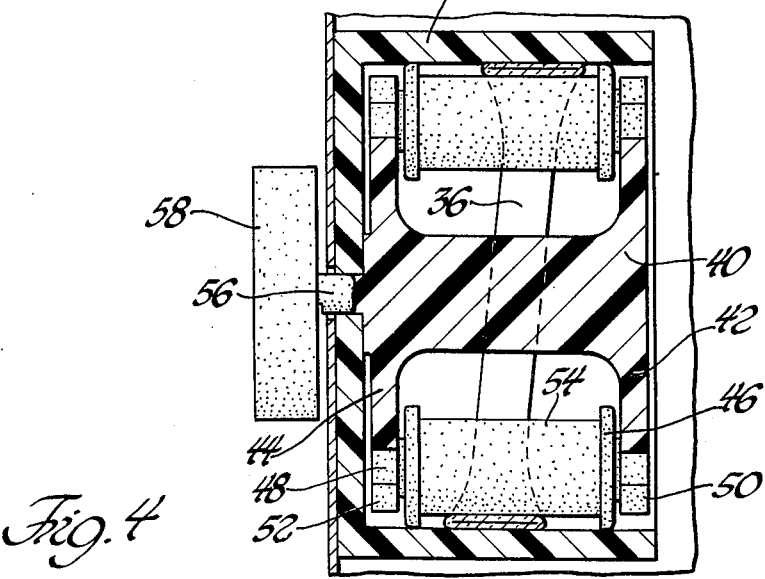
FIG. 4 is a view taken on the line 4—4 of FIG. 3.

Within the housing is a rotatable member 40 having two identical pairs of parallel arms, the pairs being 180° apart, one pair of arms being shown at 42 and 44 (see FIG. 4). At the outer end of each pair of arms is a roller 46 having a shaft 48 the ends of which are in elongated notches 50 and 52 in the ends of the arms. The outer surface of each of the rollers is formed by a sleeve 54 of a rubber or a like material. Hence, the rollers are in resiliently biased contact with the center portion 36 of the tube so that each of the rollers collapses and thereby closes the tube in the area of contact of the roller with the tube. Connected to the rotatable member by the shaft 56 of the rotatable member is a knob 58 which constitutes means for selectively actuating the pump to either pump air into the chamber or out of the chamber. That is, when the knob, and therefore also the rotatable member, is turned in one direction, each of the rollers, as it rolls along in resiliently biased contact with the tube, squeezes the tube closed in the area of the contact of the roller with the tube and thereby squeezes or pumps the air through the air passage, comprising the tubes 24 and 22, into the air pocket in the top of the drip chamber. On the other hand, when the knob is turned in the other direction, the resulting rotation of the rotatable member and its associated rollers causes the air to be pumped out of the drip chamber. At any given time the drip chamber is sealed from the atmosphere, and hence the drip chamber pressure can be as selected and different from the ambient atmospheric pressure, this because the rollers are in biased contact with the tube portion 36 to squeeze it closed. But because the end 38 of the tube 28 is open to the atmosphere, air can be pumped from the atmosphere into the drip chamber or from the drip chamber into the atmosphere.

Before further describing the operation of and procedure for using the invention, it is appropriate, for purposes of comparison, to describe the procedure for using a system incorporating a conventional drip chamber, i.e. one requiring employment of a hypodermic needle.

In setting up any extracorporeal blood circulation system, the first step, after all the components are joined by the tube set, is to prime the entire system with a sterile saline solution. That is, all air, save for some in the drip chamber, is purged from the system by way of filling it with the sterile saline solution. With a system containing the conventional drip chamber, it is the usual practice for the medical attendant to maneuver the drip chamber through vertical and horizontal orientations until finally, with the drip chamber oriented vertically, there is the correct amount of air at the top of the drip chamber. With this accomplished and with the inlet and outlet ends of the system having been secured into the patient's bloodstream, the blood pump of the system is actuated and the patient's blood is thereby caused to work its way through the system until all the saline solution has been displaced. From then on, as the system operates, if the blood level in the drip chamber drops below or rises above the prescribed level, the medical attendant injects the hypodermic needle of a syringe into the drip chamber and either withdraws or injects air, as needed. This procedure is difficult, cumbersome and involves some hazard, as aforesaid, even for a skilled medical attendant and all the more so if the patient is required to perform it.

With the system of the present invention, there is no need or reason for maneuvering the drip chamber through various orientations to attain the proper amount of air in the drip chamber. Rather, with the sterile saline solution in the system the drip chamber can immediately be placed or left in a vertical position without concern whether it contains too much air or too little air. With the drip chamber in its vertical position, if it contains too little air, it is simply a matter of turning knob 58 in a direction to pump air into the chamber, until the proper level is attained. On the other hand, if the drip chamber contains too much air, then the knob 58 is turned in the other direction thereby pumping air out of the drip chamber until the proper level is attained. At any time later, during circulation of the patient's blood through the system, if the blood level in the drip chamber falls below or rises above the prescribed limits, it again is simply a matter of turning the knob 58 clockwise or counterclockwise, depending on need, to pump air into or out of the drip chamber.

Albeit the air passage communicates with the drip chamber through the top wall of the chamber, there remains the possibility, as by way of some manipulative error in the use of the system, that blood, or the salin solution, might enter into the passage from the drip chamber. This does no harm to the system if the liquid is prevented from flowing into the transducer or into the air pumping portion of the passage. To assure against any flow of liquid into these parts of the system, a hydrophobic filter 60 is included in the tube 22. This filter allows the free passage of air therethrough but blocks the flow of liquid, and therefore the flow of blood or saline solution. Hydrophobic filter materials are well known and easily available in the market, an example being that currently being marketed under the trademark "Acropor" by the Gelman Instrument Company of Ann Arbor, Michigan, Acropor being a microporous hydrophobic organic polymer membrane filter of about 0.45 microns pore size.

Also well known and available in the market are suitable transducers for measuring gas pressure and hence for use as element 26. It should be mentioned that the measurement of the air pressure, by transducer 26, constitutes measurement of the blood pressure in the extracorporeal blood circulation system, such measurement being desirable to assure rapid detection of any abnormal increase or decrease in the pressure within the system.

It will be understood that while the invention has been described particularly with reference to a preferred embodiment thereof, various changes and modifications may be made all within the full and intended scope of the claims which follow.

The embodiments of the invention in which an exclusive property or privilege is claimed are defined as follows:

1. An extracorporeal blood circulation system comprising tubing for conducting blood to and from a patient and including a chamber having a blood inlet at the top thereof and a blood outlet at the bottom thereof, said chamber during operation containing blood in its bottom portion and air in its top portion, an air passage communicating at one end thereof with the top portion of the chamber, an air pump communicating with said passage for pumping air through said passage from the chamber into the atmosphere or from the atmosphere into the chamber, and means for selectively actuating the pump to either pump air into or out of the chamber, said pump sealing said chamber from the atmosphere when said pump is not in operation.

2. A system as set forth in claim 1 wherein said air pump is a roller pump comprising a housing having a cylindrical wall receiving thereagainst a flexible tube, and a rotor in said housing having at least one rotatable roller secured thereto and resiliently biased against said flexible tube and rollable along said flexible tube when said rotor is rotated.

3. A system as set forth in claim 1 wherein said passage includes a hydrophobic filter.

* * * * *